(12) United States Patent
Mains, Jr.

(10) Patent No.: US 11,291,724 B2
(45) Date of Patent: Apr. 5, 2022

(54) METHOD, APPARATUS AND SYSTEMS FOR TRACKING FREIGHT

(71) Applicant: CRC R&D, LLC, Kenner, LA (US)

(72) Inventor: Ronald H. Mains, Jr., Kenner, LA (US)

(73) Assignee: CRC R&D, LLC, Kenner, LA (US)

( * ) Notice: Subject to any disclaimer, the term of this patent is extended or adjusted under 35 U.S.C. 154(b) by 0 days.

(21) Appl. No.: 17/012,717

(22) Filed: Sep. 4, 2020

(65) Prior Publication Data
US 2020/0397897 A1 Dec. 24, 2020

Related U.S. Application Data

(63) Continuation of application No. 16/029,409, filed on Jul. 6, 2018, now Pat. No. 10,772,957, which is a
(Continued)

(51) Int. Cl.
*A61K 39/39* (2006.01)
*A61K 39/395* (2006.01)
(Continued)

(52) U.S. Cl.
CPC .... *A61K 39/3955* (2013.01); *C07K 14/70578* (2013.01); *C07K 16/2875* (2013.01);
(Continued)

(58) Field of Classification Search
CPC .................................................. A61K 39/3955
See application file for complete search history.

(56) References Cited

U.S. PATENT DOCUMENTS 5,712,789 A * 1/1998 Radican ................. G06Q 10/08
700/226
6,556,138 B1 * 4/2003 Sliva ..................... B65F 1/1484
340/545.6
(Continued)

FOREIGN PATENT DOCUMENTS

WO 2006084255 8/2006

OTHER PUBLICATIONS

ITS International, Savings accrue from on-line form truck Screening, Dec. 8, 2013, https://web.archive.org/web/20131208174419/https://www.itsinternational.com/sections/cost-benefit-analysis/features/savings-accrue-from-on-line-from-truck-screening/ (Year: 2013).
(Continued)

*Primary Examiner* — Travis R Runnings
(74) *Attorney, Agent, or Firm* — Jason P. Mueller; FisherBroyles, LLP

(57) ABSTRACT

Methods, apparatus, and systems are provided for tracking freight. Embodiments include a tracking device for a trailer containing a load. The tracking device includes a support member, a connector, a housing and a GPS tracker configured to track the location of the load. The connector securely attaches to a container on the trailer and attaches to a seal such that the container cannot be opened without breaking the seal. The support member stabilizes the housing and protects the tracking device during transit of the load. A tracking system may implement to monitor, gather information and report on the tracking device and the load.

20 Claims, 11 Drawing Sheets

Related U.S. Application Data continuation of application No. 14/521,361, filed on Oct. 22, 2014, now Pat. No. 10,019,878.

(60) Provisional application No. 62/064,331, filed on Oct. 15, 2014.

(51) Int. Cl.

| | |
|---|---|
| *H04W 4/029* | (2018.01) |
| *G06Q 10/08* | (2012.01) |
| *G08B 13/24* | (2006.01) |
| *C07K 14/705* | (2006.01) |
| *C07K 16/28* | (2006.01) |
| *A61K 38/00* | (2006.01) |
| *A61K 39/00* | (2006.01) |

(52) U.S. Cl.
CPC ......... *G06Q 10/08* (2013.01); *G06Q 10/0833* (2013.01); *G08B 13/2434* (2013.01); *G08B 13/2462* (2013.01); *H04W 4/029* (2018.02); *A61K 38/00* (2013.01); *A61K 2039/505* (2013.01); *C07K 2317/52* (2013.01); *C07K 2319/30* (2013.01)

(56) References Cited

U.S. PATENT DOCUMENTS

| | | | | |
|---|---|---|---|---|
| 7,312,702 | B1* | 12/2007 | Willms | G06Q 10/08 340/540 |
| 8,219,503 | B2* | 7/2012 | Takahashi | G06Q 10/087 705/330 |
| 8,279,067 | B2* | 10/2012 | Berger | H04W 60/00 340/572.1 |
| 10,019,878 | B2* | 7/2018 | Mains, Jr. | G08B 13/2434 |
| 10,127,556 | B2 | 11/2018 | Lesesky | |
| 2003/0063000 | A1* | 4/2003 | Grimm | G08B 13/14 340/568.7 |
| 2004/0155778 | A1* | 8/2004 | Shek | G08B 13/2417 340/572.1 |
| 2005/0071247 | A1* | 3/2005 | Kelley | G06Q 10/08 705/330 |
| 2005/0116833 | A1* | 6/2005 | Miller | G01M 5/0008 340/690 |
| 2005/0231365 | A1* | 10/2005 | Tester | G06K 19/07798 340/568.1 |
| 2006/0109106 | A1* | 5/2006 | Braun | G06Q 10/08 340/539.13 |
| 2009/0032510 | A1 | 2/2009 | Ando | |
| 2009/0265223 | A1 | 10/2009 | Takahashi | |
| 2009/0322510 | A1* | 12/2009 | Berger | G06Q 10/0833 340/539.1 |
| 2011/0128143 | A1* | 6/2011 | Daniel | G08B 21/0269 340/539.1 |
| 2011/0133888 | A1* | 6/2011 | Stevens | G06Q 10/0833 340/8.1 |
| 2011/0133932 | A1* | 6/2011 | Tan | G09F 3/0329 340/568.1 |
| 2013/0016636 | A1 | 1/2013 | Berger | |
| 2014/0006302 | A1 | 1/2014 | Mcquillan | |
| 2014/0067313 | A1* | 3/2014 | Breed | G01P 15/02 702/141 |
| 2014/0218218 | A1* | 8/2014 | Lloreda | E05B 83/08 340/989 |
| 2015/0081582 | A1 | 3/2015 | Mains, Jr. | |

OTHER PUBLICATIONS

"Big Bend Travel Plaza: Driver Services", published by wwww.bigbendtravelplaza.com on Jan. 8, 2011 (Year 2011).

* cited by examiner

| Customer | BOL | Origin | Destination | Appointment Time | ETA | Status |
|---|---|---|---|---|---|---|
| Customer A | 10000 | Geismar, LA | Decatur, TX | 9/25/2014 3:42:49 PM | 9/26/2014 6:19:40 PM | Late |
| Customer A | 10001 | Geismar, LA | Decatur, TX | 9/25/2014 11:48:21 AM | 9/26/2014 6:32:00 AM | Late |
| Customer A | 10002 | Geismar, LA | Decatur, TX | 9/25/2014 7:00:02 PM | 9/26/2014 11:47:44 AM | On Time |
| Customer A | 10003 | Geismar, LA | Decatur, TX | 9/27/2014 4:21:16 AM | 9/26/2014 8:31:33 AM | Late |
| Customer A | 10004 | Geismar, LA | Decatur, TX | 9/25/2014 4:07:07 PM | 9/26/2014 8:55:19 AM | On Time |
| Customer A | 10005 | Geismar, LA | Decatur, TX | 9/27/2014 8:36:10 AM | 9/26/2014 3:17:32 PM | On Time |
| Customer A | 10006 | Geismar, LA | Decatur, TX | 9/26/2014 5:49:16 AM | 9/26/2014 9:55:38 PM | Late |
| Customer A | 10007 | Geismar, LA | Decatur, TX | 9/25/2014 5:48:51 PM | 9/26/2014 10:03:47 AM | Late |
| Customer A | 10008 | Geismar, LA | Decatur, TX | 9/25/2014 2:03:22 PM | 9/26/2014 2:43:25 PM | Late |
| Customer A | 10009 | Geismar, LA | Decatur, TX | 9/27/2014 12:02:16 AM | 9/26/2014 8:42:02 PM | On Time |

Showing 1 to 10 of 10 entries

METHOD, APPARATUS AND SYSTEMS FOR TRACKING FREIGHT

CROSS-REFERENCE TO RELATED APPLICATIONS

This application is a continuation of U.S. patent application Ser. No. 16/029,409, filed Jul. 6, 2018, which is a continuation of U.S. patent application Ser. No. 14/521,361, filed on Oct. 22, 2014, now U.S. Pat. No. 10,019,878, which claims the benefit of U.S. Provisional Patent Application No. 62/064,331 filed on Oct. 15, 2014, the entire contents of each of which are incorporated herein by reference.

FIELD

The present invention relates to methods, apparatuses, and systems for the tracking of freight, and in particular though non-limiting embodiments, to methods, apparatus, and systems for tracking sealed trucks and containers by global position systems ("GPS") via wireless communication.

BACKGROUND

GPS systems and mobile tracking applications are used to track freight in the transportation industry. Many existing systems, however, are prone to error for various reasons. Common problems include: durability and operability under adverse conditions; functionality in directly tracking a container containing cargo; and security. Regarding durability and operability, existing systems have typically not included housings capable of withstanding the swaying, bumps, wind, weather and other adverse conditions often encountered during truck transport. Regarding functionality, existing systems may provide incorrect information as to location of the actual load being transported because they are connected to the tractor and/or driver and are not connected to the actual container housing the cargo. Indeed, it is not uncommon for existing systems to be hardwired to freight hauling tractors and/or linked to a driver's cell phone. Regarding security, existing systems may be tampered with and are typically not integrated with existing security systems for the container housing the cargo.

SUMMARY

Embodiments of the present invention address the problems described above with respect to existing GPS receiver systems and mobile tracking applications that have been used to track freight in the transportation industry. Indeed, the present invention provides for new and improved methods, apparatuses and systems for tracking freight.

In an example embodiment of the present invention a system is provided that includes a removable tracking device; a seal; and a container. The tracking device is integrated with and/or securely attached to the seal and/or the container such that the container cannot be accessed without breaking the seal.

In another example embodiment of the present invention, a system for broker trucking is provided that includes at least one container including a load, a removable tracking device configured to continuously transmit a location of the container, the container sealed with a seal to prevent access to the load and tracking device without breaking the seal; a computer configured to continuously receive the location of the container from the respective removable tracking device; and a user interface configured to display the transmitted location of the at least one container as received by the computer to an administrator.

In yet another embodiment of the present invention, a method of broker trucking is provided that includes the following steps: obtaining a tracking device and a bill of lading for a load; loading a container, connected to a trailer, with the load; sealing the container such that neither the load, tracking device or bill of lading can be accessed without breaking the seal; monitoring the container while the load is in transit; breaking the sealed container upon the arrival at a place of load delivery; removing the load from the container; and returning the tracking device and the bill of lading to a depository. In yet another embodiment of the present invention, a tracking device for a trailer containing a load is provided that includes a support member, a connector, and a main body/housing enclosing a GPS tracker configured to track the location of the load. The connector is connected to the support member, the support member is connected to the main body and the GPS tracker is located within the main body. The connector securely attaches to a container on the trailer and attaches to a seal such that the container cannot be opened without breaking the seal. The support member stabilizes the housing and protects the tracking device during transit of the load.

DESCRIPTION OF DRAWINGS

FIG. 12 is a search screen with textual reporting of the tracking system, according to an exemplary embodiment of the present invention.

FIG. 13 is an administration screen of the tracking system, according to an exemplary embodiment of the present invention.

DESCRIPTION

The present invention provides methods, apparatuses, and systems for tracking of freight, including methods, apparatuses, and systems for tracking sealed trucks and containers by GPS via wireless communication.

According to an example embodiment of the present invention, a truck pulls up to a warehouse. Personnel greet the driver and load a trailer with appropriate freight and provide a bill of lading to the driver. Closing the trailer and/or container loading door(s) the personnel lock the load with a tracking device such that the tracking device is secured to the door(s) and a seal. The tracking device cannot be removed, or the door(s) opened, without breaking the seal. With the trailer loaded, secured and ready to depart, personnel approach a local terminal notifying a tracking system that the load is ready to depart or has departed. The tracking system processes the notification and initiates freight load tracking. The tracking system gathers information during transit of the load and processes the information for use by administrators. The administrators may monitor the load, update arrival times, connection times, and customers as to the status of the load. Once the load arrives at its destination, personnel break the seal, unload the trailer or container, and update the tracking system accordingly. The destination warehouse then forwards the tracking device to an appropriate location.

In various embodiments, the tracking system includes a container/trailer and tracking device configured to securely and universally integrate with existing load seals. The tracking device houses electronic circuitry and microcontrollers (mainboard, accelerometer, GPS tracker, GSM communication, power supply, satellite communication, optional additional sensors—e.g. temperature, vibration, and seal) and interfaces with a tracking system that may be web based. The tracking device electronic circuit board/s collect/transmit acceleration and GPS data to the web application via GSM and/or satellite communication. The tracking device and/or tracking system provide an administrator with tracking data which may be utilized for various purposes, including administration, reporting, and searching. This data may be automatically or manually entered into an existing company Transportation Management System.

Figure 1:
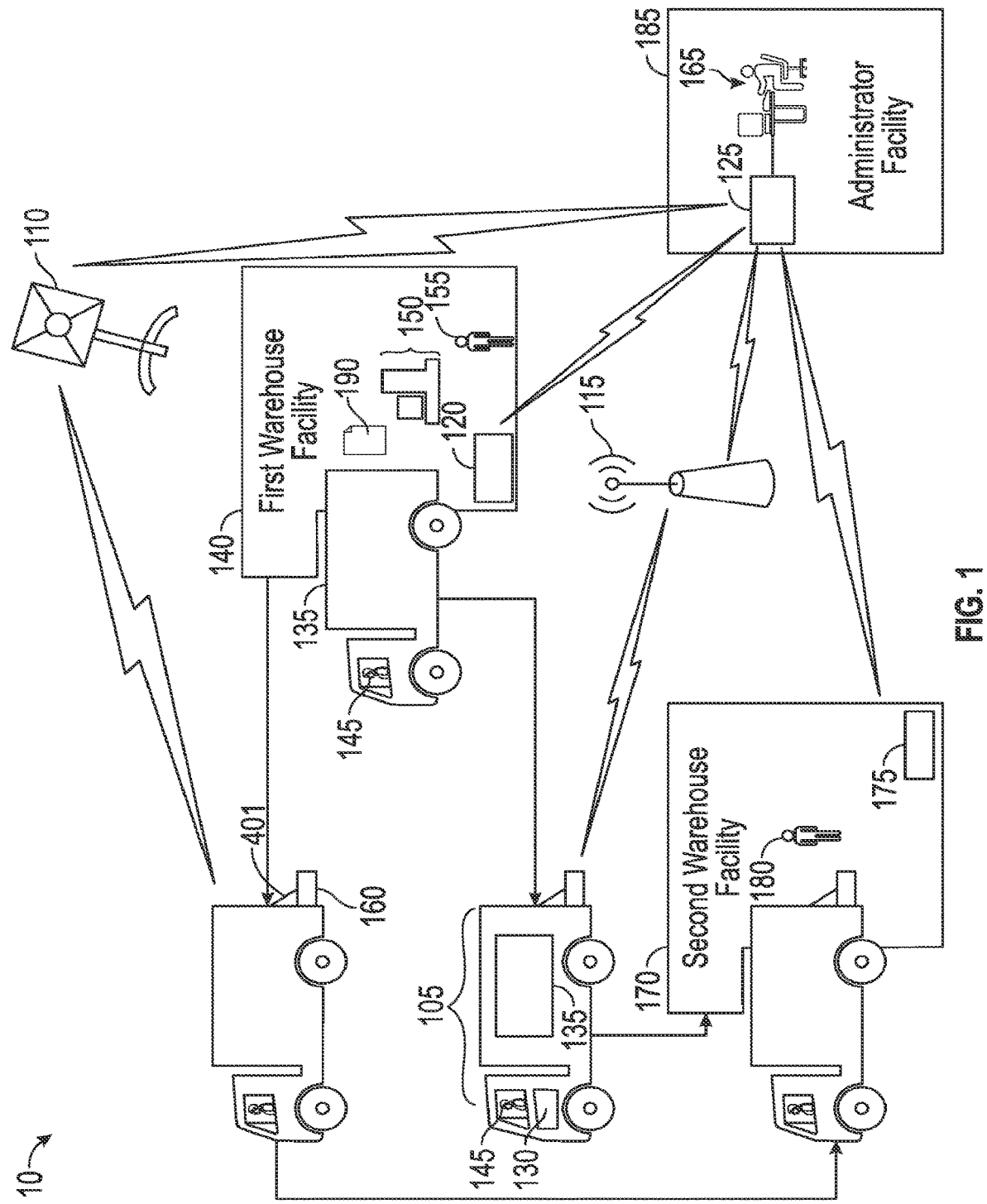
FIG. 1 is a schematic overview of a freight tracking system, according to an exemplary embodiment of the present invention.

FIG. 1 schematically depicts a tracking system (10) including warehouses (140, 170), a bill of lading (190), a container (135), bolt seal (401) and a tracking device (160). In various embodiments of the present invention the system may include greater or fewer components. At a first warehouse facility (140) a bill of lading (190) is given to driver (145) and load (150) is loaded into a trailer (135) (or a container located on the trailer) by warehouse personnel (155). The trailer/container and tracking device (160) are placed together and then a seal is used to secure the load. In one embodiment the trailer/container includes doors that are latched together with overlapping flanges that include a central hole. Tracking device (160) includes a connector that attaches to the overlapping flanges of the doors and includes an aperture that aligns with the central hole of the doors. The seal may be a bolt seal that passes through the hole in the door flanges and the aperture in tracking device (160). An end piece is then placed on the seal such that the doors, tracking device and seal are secured together. The doors cannot be opened and the tracking device (160) cannot be removed and/or tampered with without breaking the seal. Warehouse personnel (155) may then input into a tracking system that the load is ready to leave local terminal (125) and activate tracking. The trailer (135) departs the first warehouse and while in transit via GSM (115) and/or satellite (110) continuously informs the tracking system computer (125) of the trailer/containers (135) position. Once the trailer (135) arrives at a second warehouse facility (170), warehouse personnel (180) unload the load (150). After unloading, personnel update a terminal (175) deactivating tracking system tracking by the tracking system computer (125).

The system of the present disclosure may include a first (140), second (170), or further plurality of warehouse facilities. Furthermore, the warehouse facilities are not limited to enclosed truck freight logistic centers but may include docks, ships, or other facilities where efficient routing of cargo/freight is advantageous.

The bill of lading (190) of the present disclosure can take physical or digital forms documenting the cargo while giving title to a specified party (e.g. delivery warehouse operator). The bill of lading can be stored at various warehouse facilities and/or digitally within the tracking device itself.

The trailer/container of the present disclosure can vary based on different embodiments. In some instances a container is attached to a trailer and pulled by a tractor. In other instances the container is part of the trailer and is pulled by a tractor. In other instances the tractor, trailer and container are one unit. In other instances the container may be a shipping container, smaller container or the like that may be loaded on ships or other forms of transport such as cargo planes and helicopters.

Figure 2:
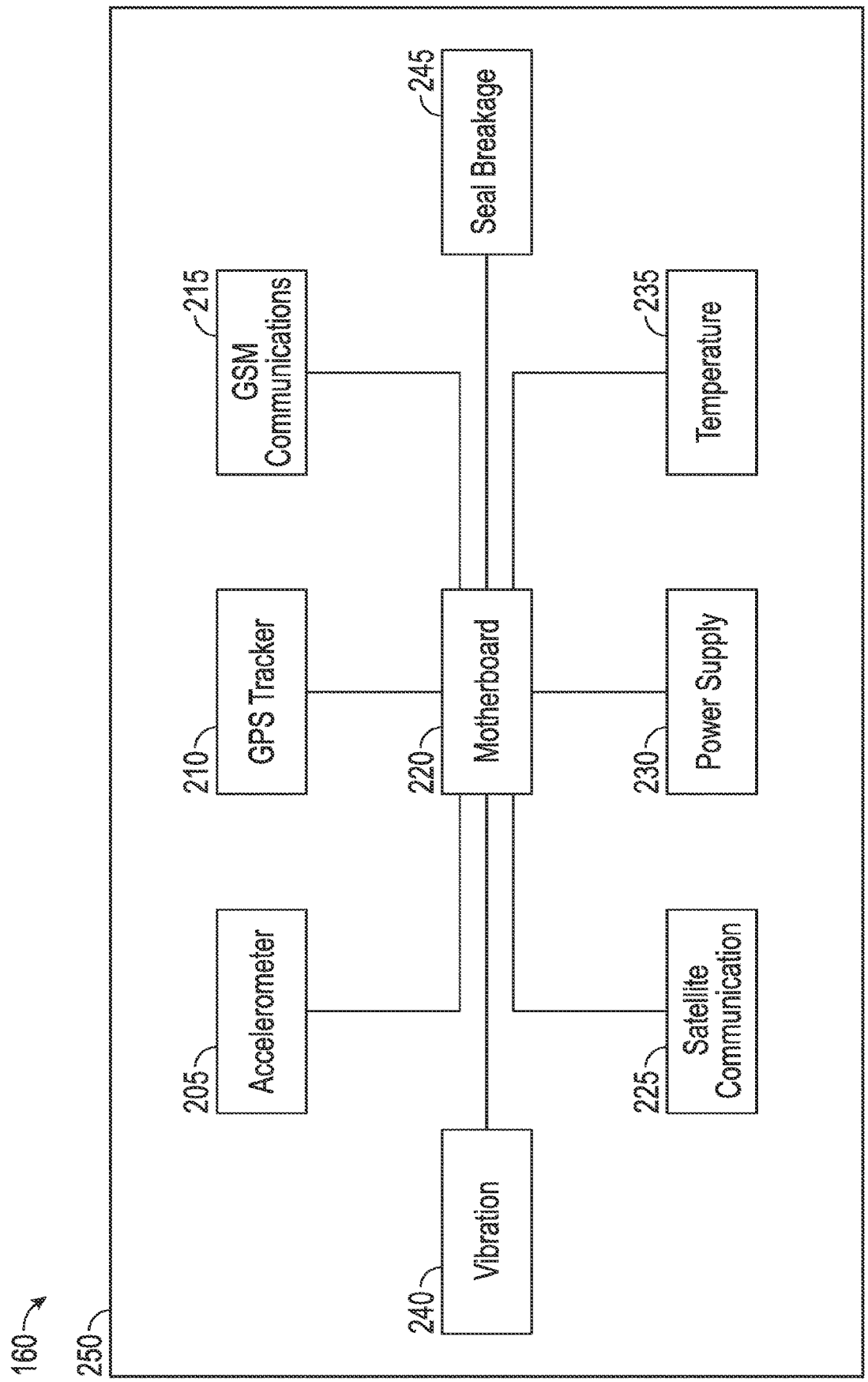
FIG. 2 is a schematic of a tracking device, according to an exemplary embodiment of the present invention.

In various embodiments of the system the tracking device (160) can take many forms. FIG. 2 shows a schematic of a tracking device (160) according to an exemplary embodiment of the present invention. As depicted, the tracking device (160) includes accelerometer (205), GPS tracker (210), GSM communications (215), satellite communications (225), power supply (230) and temperature (235), vibration (240), and seal breakage (245) sensors operably connected to a mainboard, and located within a housing (250). In various embodiments the tracking device (160) may include greater or fewer components and may be configured to weigh less than ten pounds.

The accelerometer (205) can provide local acceleration information to the system. The accelerometer (205) can indicate whether the velocity of the tracking device (160) is increasing or decreasing. For example, in a high wind environment, the device (160) may sway causing damage to the components and/or container cargo. The accelerometer (205) may log and monitor these local stresses. The accelerometer (205) can be, as pictured in FIG. 3, a LIS344AL (305). A LIS344AL (305) is a low-power three axis linear accelerometer that includes a sensing element and analog IC interface.

For monitoring the tracking device (160) position, a GPS tracker (210) can be included in an embodiment of the present invention. The GPS tracker (210) can be connected to a variety of systems including but not limited to the Global Positioning System ("GPS"), the Global Navigation Satellite System ("GLONASS"), and/or the BeiDou Navigation Satellite System. The GPS tracker (210) has the ability to receive information concerning the latitudinal and longitudinal position of the tracking device (160). The GPS tracker may also be configured to translate received latitudinal and longitudinal information into velocity and acceleration. The GPS tracker (210) can comprise a Ultimate GPS Module (310) as pictured in FIG. 3 and built around the MTK3339 chipset.

Figure 3:
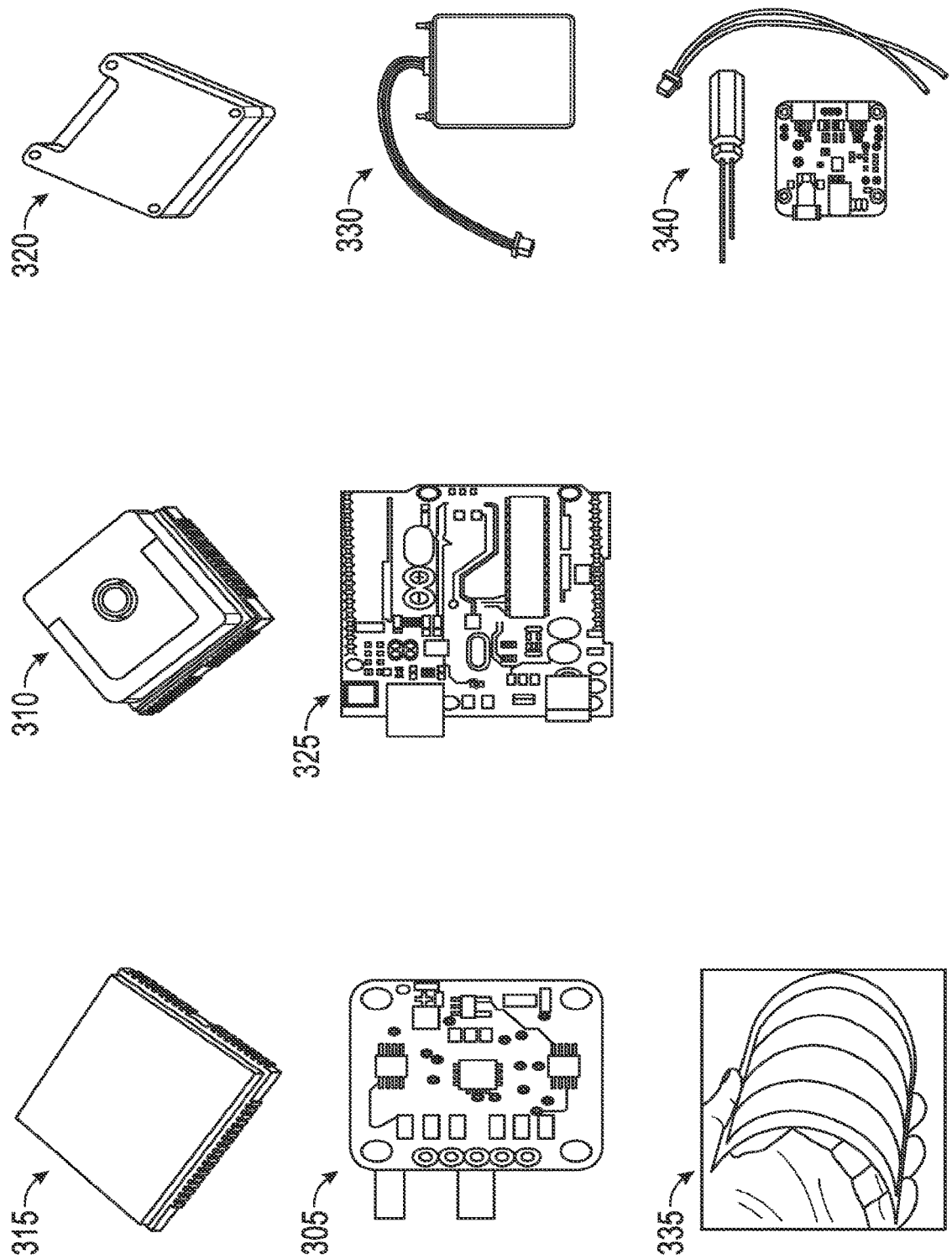
FIG. 3 shows images of potential components of the tracking device shown in FIG. 2.

In embodiments of the present invention the tracking device can be grouped into two versions, a version with satellite communication (225) and a version without satellite communication. A device without satellite communication can communicate with the system via GSM mobile phone networks, but cannot communicate in areas where a GSM mobile phone network is not available. The GSM communications (215) can be for instance a Quectel Quad-band GSM/GPRS M10 Microcontroller (315) as pictured in FIG. 3. On the other hand a tracking device with satellite communication (225) can use GSM mobile phone networks (primary mode of communication) and the Iridium satellite phone network (secondary mode of communication). This allows continuous feedback to the tracking system on transit legs with little to no coverage such as vessel or train. Satellite communications (225) can be a variety of different components such as for instance an Iridium 9602 Satellite Modem (320) as seen in FIG. 3. The Iridium 9602 SBD transceiver (320) provides global tracking via the Iridium satellite network.

The accelerometer (205), GPS tracker (210), GSM communications (215), and satellite communications (225) may be operably connected to a mainboard (220). The mainboard (220) can allow processing of information from the GPS tracker (210) concerning the location of the tracking device (160) and forwarding to the tracking system of said information through the appropriate communications link, e.g. GSM (215) or satellite (220). The mainboard (220) can detect the presence or absence of a GSM signal and thereby can control whether the tracking device forwards location information (e.g. from the GPS tracker (210)) to the system via GSM (215) or satellite communication (225). In various instances the mainboard (220) may encrypt or otherwise protect the tracking information transmitted to prevent interference thereto. The mainboard (220) may be associated with an identifying ID that allows the system to identify the tracking device. In various instances, the mainboard (220) may be partially integrated with each of the various components of the tracking device (160) or may comprise a separate component. In various embodiments the mainboard (220) may take many forms, for example, an Arduino UNO Rev3 (325) as shown in FIG. 3.

Power for the mainboard (220), accelerometer (205), GPS tracker (210), GSM communications (215) and satellite communications (225) and/or other components of the tracking device can flow directly from the power supply (230) to the individual components or via the mainboard (220). In various instances the power supply (230) may be configured to send to the tracking system via the mainboard (220) and communications indications of remaining power. In various instances power will be continuous or it may be regulated by a switch or other mechanism. The power supply (230) can take on a variety of different forms, such as a battery, depending on the design of the tracking device (160). In an embodiment the power supply (230) is a Lithium Ion Polymer Battery—3.7 v 1200 mAh (330) as shown in FIG. 3. In an additional embodiment the power supply (230) includes a battery as well as a solar panel to recharge the battery during daylight hours. As seen in FIG. 3 the solar panel may be a Flexible 6V 1 W Solar Panel (335) with the connection to the battery facilitated by, for example, USB/DC/Solar Lithium Ion/Polymer charger—v2 (340).

Depending on application needs, the tracking device (160) may further include additional sensors such as temperature (235), vibration (240) and seal breakage (245), all optionally connected to the mainboard (220), communications, and/or power supply (230). A temperature sensor (235) may be configured to measure the temperature outside the device (160) or inside the device (160). Vibration information can be used by the device and/or tracking system to determine cargo movement and integrity. The seal breakage sensor (245) can be connected to the bolt seal or other type of seal. In various instances the seal sensor can be a conductance based sensor such as a reed switch. A reed switch can be attached to both ends of bolt locking mechanism. When the bolt locking mechanism is locked, the circuit of the reed switch is closed and when unlocked the circuit can be opened.

The housing (250) of the tracking device (160) may be specially tailored to a unique transit application. In some instances, the tracking device may be configured to lock within existing plastic, metal, cable, or padlock seals. Alternatively, the housing (250) may be designed to lock within existing bolt seals.

The tracking system may include plastic, metal, cable, or padlock seals. These seals may be configured to pass through the aperture of the tracking device as well as the central hole of the container door overlapping flanges. These seals may include numbering unique to the load and/or customer and be configured to blush if tampered with. In some instances these seal may include a ball locking mechanism that is difficult/impossible to reseal once broken. Examples of such seals include S-13677, H-541, and H-1346 from Uline™.

Figure 4:
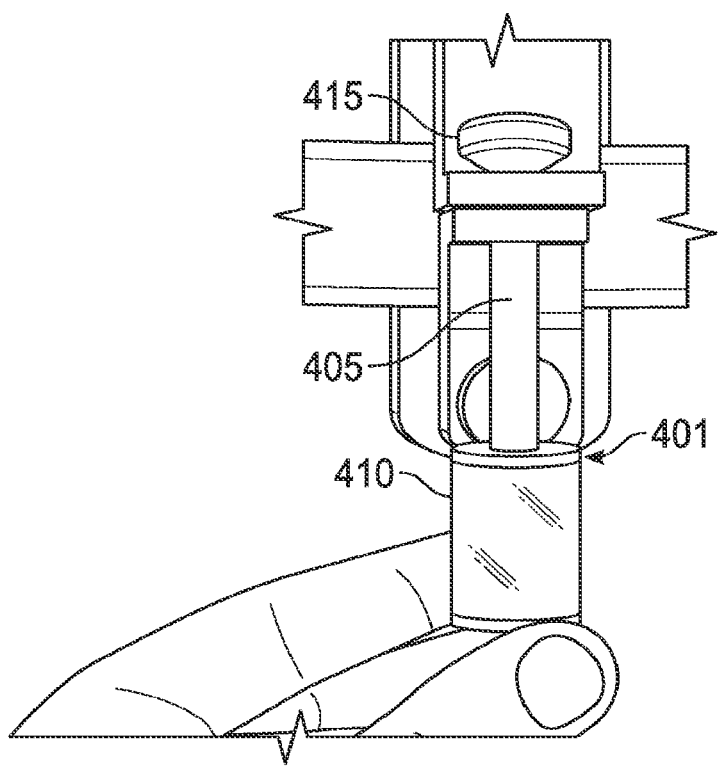
FIG. 4 shows a bolt seal.

Further embodiments of the tracking system may include a bolt seal. Bolt seals can come in a variety of forms. A commercially available bolt seal (401) can be seen in FIG. 4. Depending upon the shipping company a different bolt seal (401) may be used. The bolt seal may include numbering unique to the load and/or customer and be configured to blush if tampered with. Bolt seals can comprise a bolt (405) with a head (415) and a locking mechanism (410). The bolt seal (401) may lock the container (135) and the bill of lading (190) therein preventing access thereto without breaking of the bolt seal (401).

As seen in FIGS. 5, 6, 7, and 8, the housing may include a connector, a support member and a main body. In various embodiments, the tracking device housing may be formed from plastic (e.g. PVC), metal, or other suitable materials. The tracking device housing may include a connector that is adjustable for receiving different types of seals. The connector may be designed to attach to the seal (401) via an aperture so that the tracking device (160) cannot be removed from the seal (401) without breaking the seal. The aperture can be large enough for this purpose (401) yet small enough to derive stability for the positioning of the tracking device (160) from the seal (e.g. to limit swaying and other movement of the tracking device (160) that may damage device integrity). In various embodiments the connector (510) and connector aperture (515) can be dimensioned to fit on a bolt seal bolt (405) between the head (415) and the locking mechanism (410). In various examples a seal sensor may be tied to the aperture and extend to the connector exterior. The connector (510) may have a width of 1 inch and a thickness of 0.13 inches while the aperture (515) of the connector (510) may be 0.38 inches.

Figure 5:
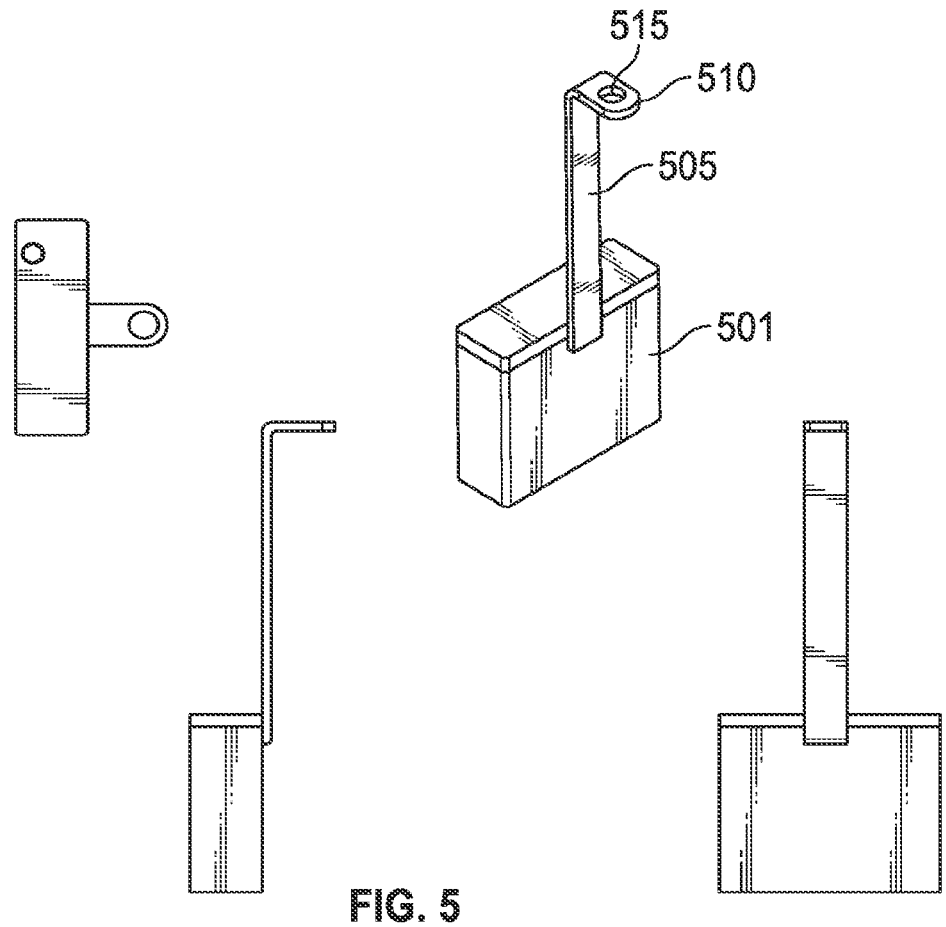
FIG. 5 shows a top, front, right, and isometric view of a housing of a tracking device, according to an exemplary embodiment of the present invention.
Figure 6:
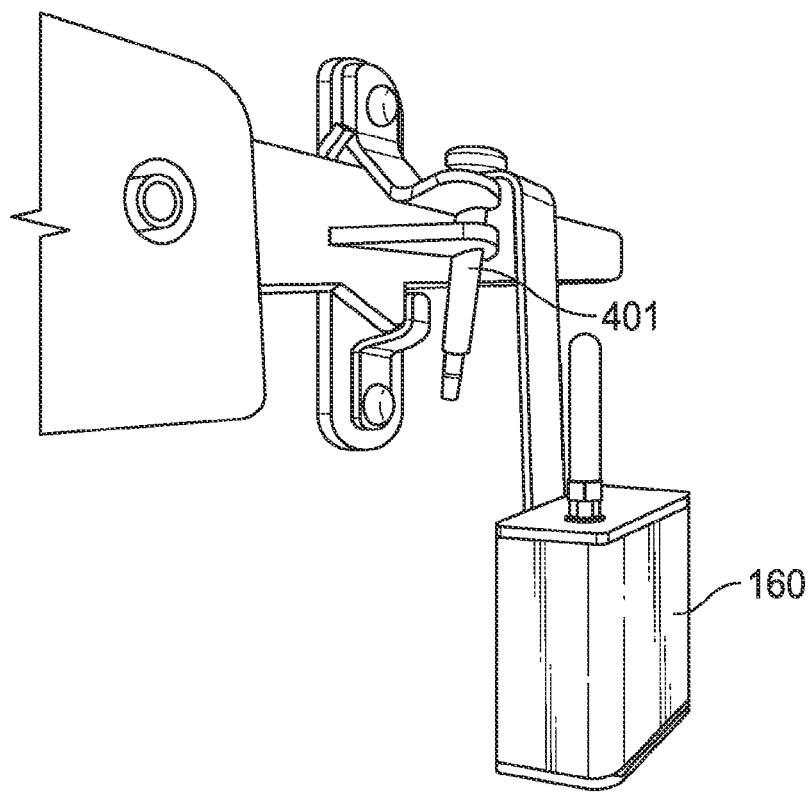
FIG. 6 shows a side view picture of a tracking device without a secured seal, accordingly to an exemplary embodiment of the present invention.
Figure 7:
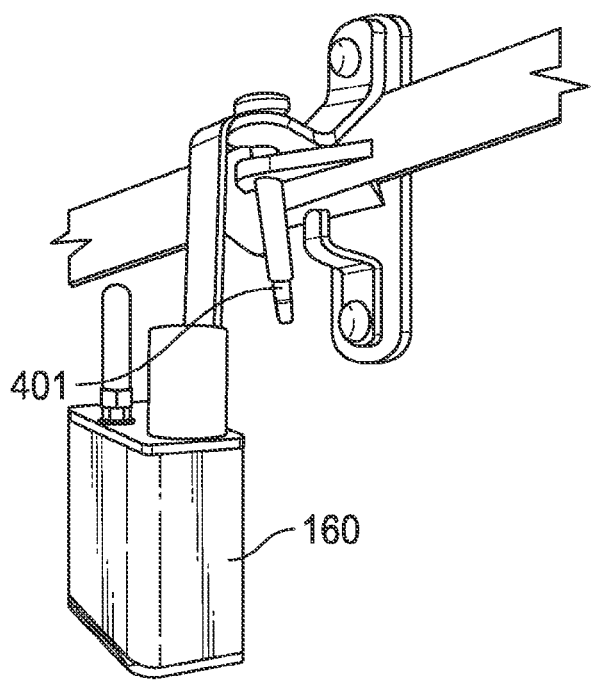
FIG. 7 shows a side view picture of the tracking device shown in FIG. 6.
Figure 8:
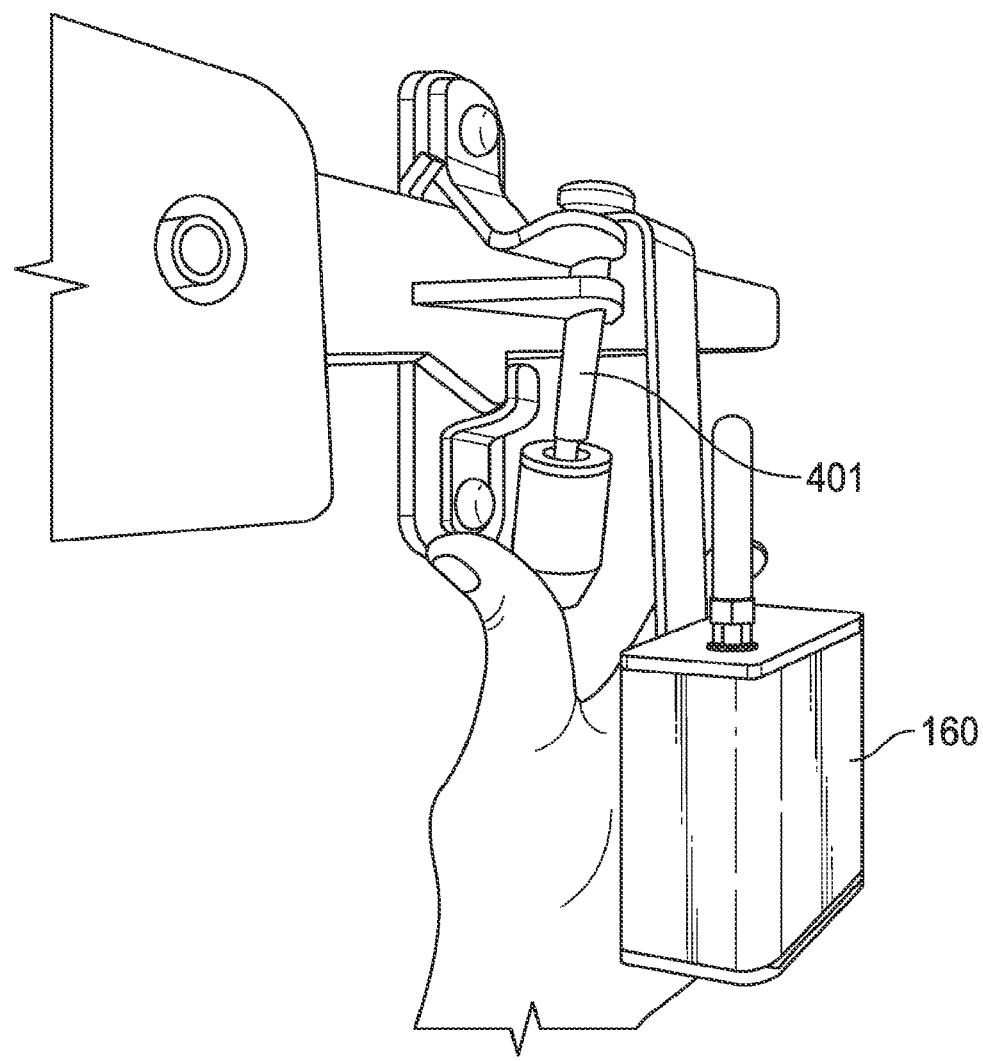
FIG. 8 shows a side view picture of the tracking device shown in FIG. 6 with the seal being secured.

The connector may be conjoined with a support member. The support member can link the connector to the housing main body. The length and geometry of the support member may vary, for example appearing arm-like and extending from a main body as seen in FIG. 5. In various embodiments the tightness of the seal connector connection and the support member's rigidity may act to limit device movement in transit. For example, as seen in FIG. 5, the support member can be linked to a connector sandwiched within the bolt seal with the integrity of the bolt seal connection and rigidity of the support member acting to substantially limit swaying and thereby protecting the tracking device integrity. The connector (505) in some instances may have a thickness of 0.13 inches and a total height of 4.5 inches including 0.5 inches of overlap with the main body (501).

The housing main body may house the mainboard and other important circuitry of the tracking device. The main body housing may take a variety of forms depending on the included circuitry and intended application. In instances the height of the housing (250) may be 6.5 inches, the main body (501) consisting of 2.5 inches and the connector (505) consisting of 4 inches. The main body (501) may have a width of 1 inch and a length of 3 inches. The tracking device may be placed on a container and continuously interact with a tracking system. The tracking system receives information from the tracking device such as latitude, longitude, acceleration, and battery life and makes said information usable to an administrator. The tracking system may include a computer (125) running software operatively connected to the tracking device (160), a user interface (185) and optionally, warehouse terminals.

The computer (125) of the tracking system may encompass any suitable processing device connected to the tracking device. The computer may be physical or web based (e.g. Amazon Web Services). Indeed the computer (125) may be adapted to execute any operating system including Linux™, UNIX™, Windows™, or any other suitable operating system. In some embodiments the computer (125) is a commercially available server, e.g. an IBM SystemxM5 Tower servers. The computer (125) may be implemented by a processor running software connected to memory and storage. Processor executes instructions, thereby communicating data from a tracking device displaying information related to the tracking, and/or manipulating data. Although described as a single processor, multiple processors may be used according to particular needs. References to processor are meant to include multiple processors where applicable. Memory and storage may include any memory or database module and may take the form of volatile or non-volatile memory including, without limitation, magnetic media, optical media, random access memory (RAM), read-only memory (ROM), removable media, or any other suitable local or remote memory component. The connection of the tracking system computer to the tracking device and/or terminals may be via the internet, internet subnetworks, such as a VPN, or via proprietary network. This connection can be hardwired to the processor or computer system, for example via cat 5 into a network card, or it can be wireless, for example GSM, satellite, or WiFi.

The terminals of the tracking system may comprise an additional desktop computer, iPad, or other network device that is capable of interacting with the tracking system computer. The terminals can be used to activate tracking by the tracking device by warehouse personnel. In other embodiments the tracking system may continuously track the tracking device.

Figure 9:
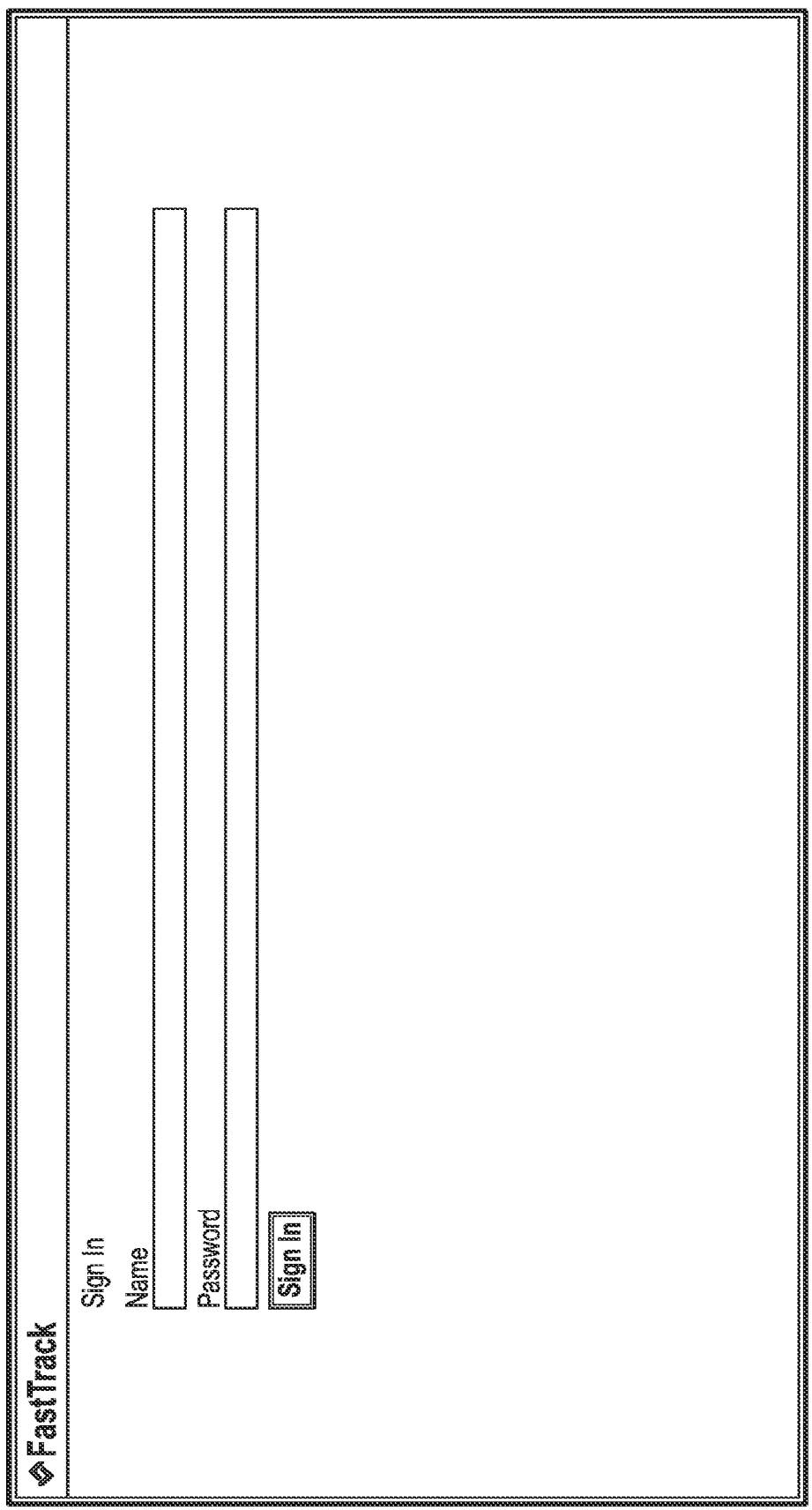
FIG. 9 is a controlled access screen of the tracking system, according to an exemplary embodiment of the present invention.
Figure 10:
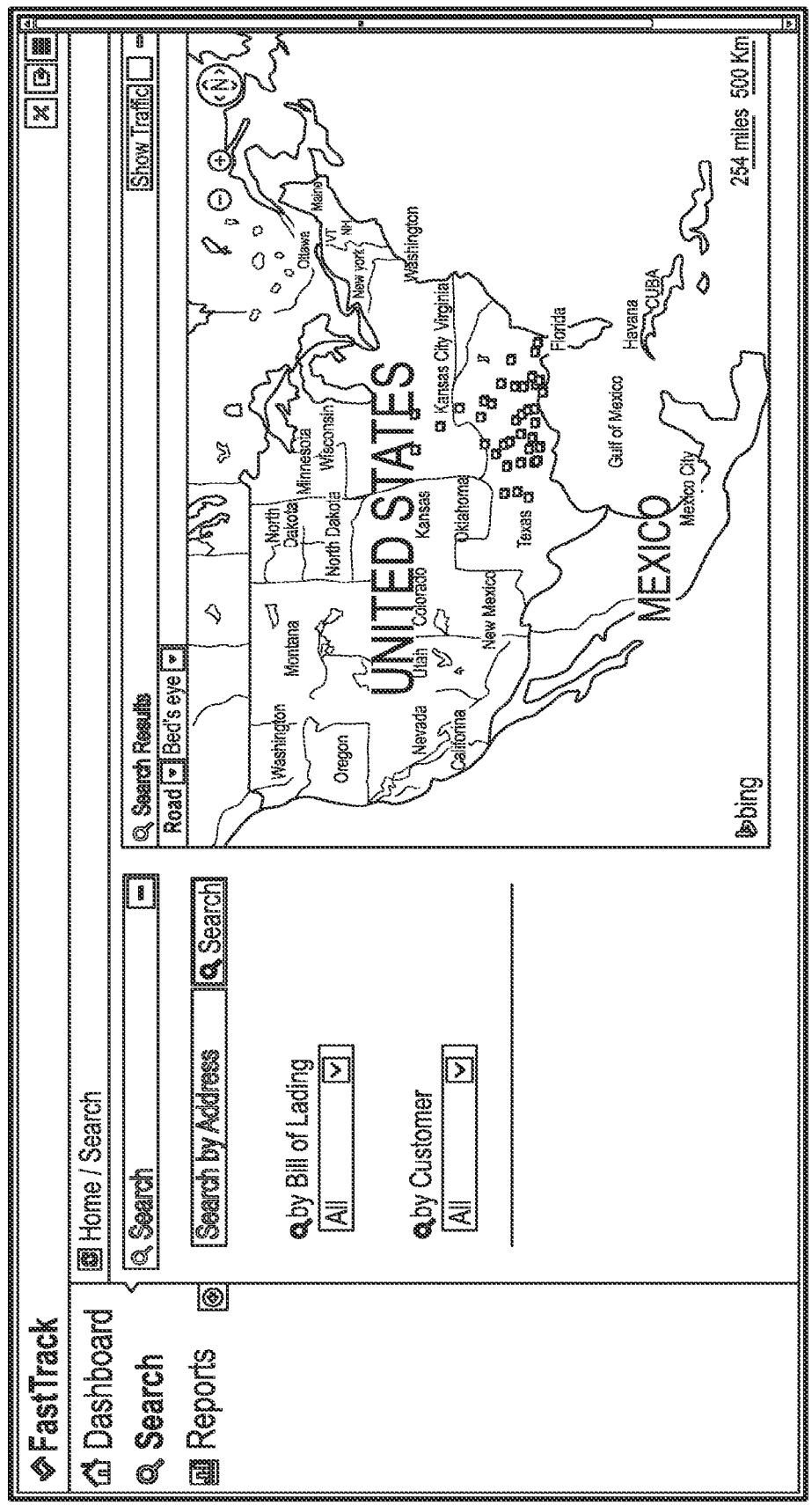
FIG. 10 is a dashboard screen of the tracking system, according to an exemplary embodiment of the present invention.
Figure 11:
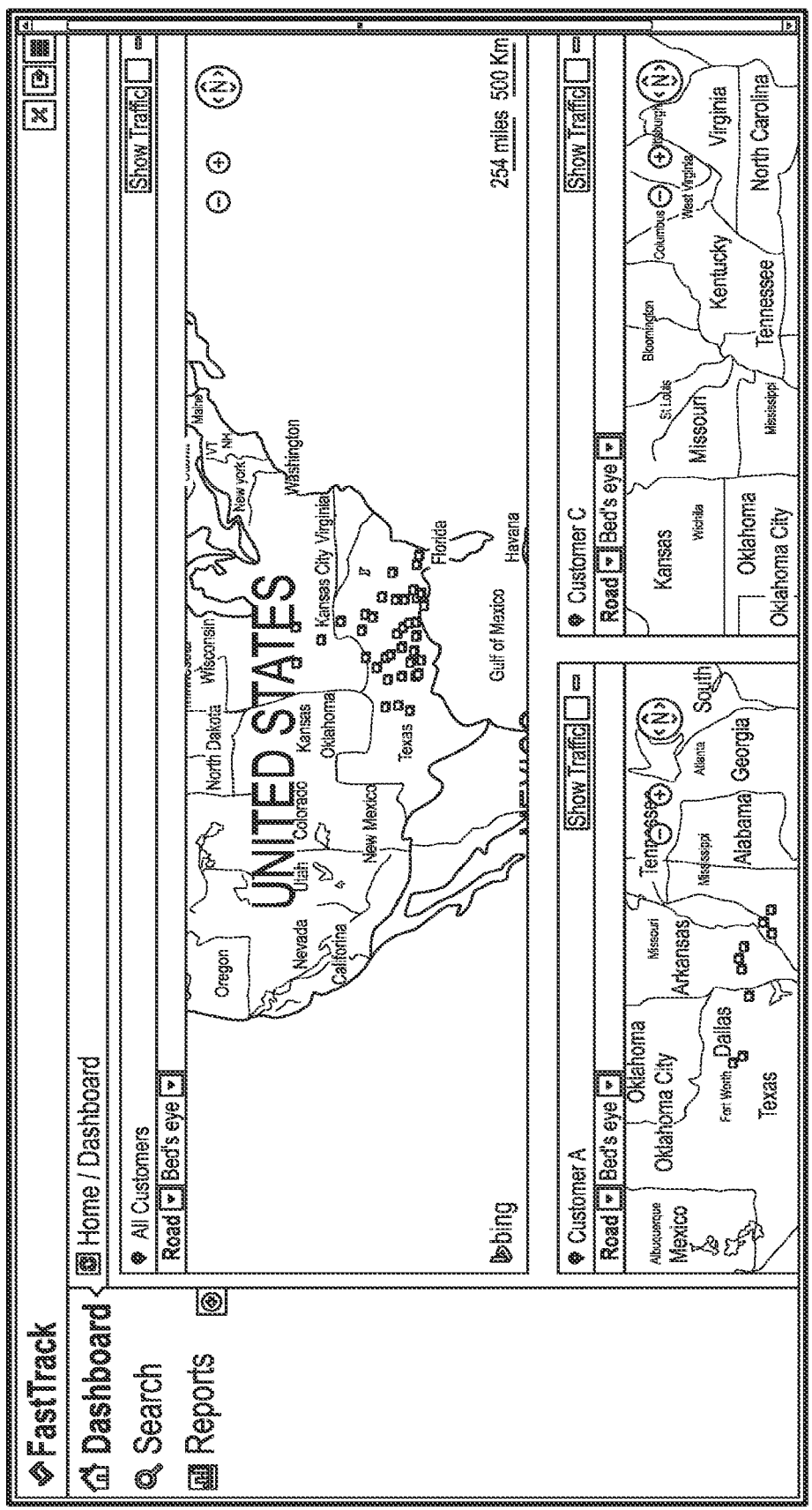
FIG. 11 is a dashboard screen of the tracking system, according to an exemplary embodiment of the present invention.

The software of the tracking system runs on the tracking system computer (125) and can include a web application. In various implementations the software may have controlled access, such as a login screen restricting administrator access as seen in FIG. 9. The software can be displayed on a user interface (185). A user interface (185) may be a monitor connected to the computer, or it may be a more remote interacting platform such as an iPad or android tablet device. In various instances the software may include a dashboard that displays maps as seen in FIGS. 10 and 11. A map displayed can be limited to various criterion such as customer or load type, or the map can display the location of all customer shipments. In various instances the software may allow multiple and/or individual maps to be displayed and certain maps to be minimized, maximized and/or rearranged. In the software the shipments can be represented on the map(s) as truck icons. The truck icons in various instances may be colored green, red, yellow or other colors to indicate shipment status (e.g., green=on schedule, yellow=behind schedule, red=late). The tracking system may establish shipment status based on estimated time of arrival ("ETA") at the destination. On land, the ETA can be derived from current shipment location, the roads (and corresponding speed limits) that must be traversed to reach the destination, and the traffic conditions on said roads. At sea, ETA can be derived from current shipment location, distance to shipment destination, and the speed of the shipment. The software may include an interactive function for the truck icons. Clicking a truck icon may result in the display of a pop-up box, which displays shipment details. The map in various embodiments may be viewed in road view or satellite view. Also, the administrator can overlay traffic data on map by click the "Show Traffic" button.

Figure 13:
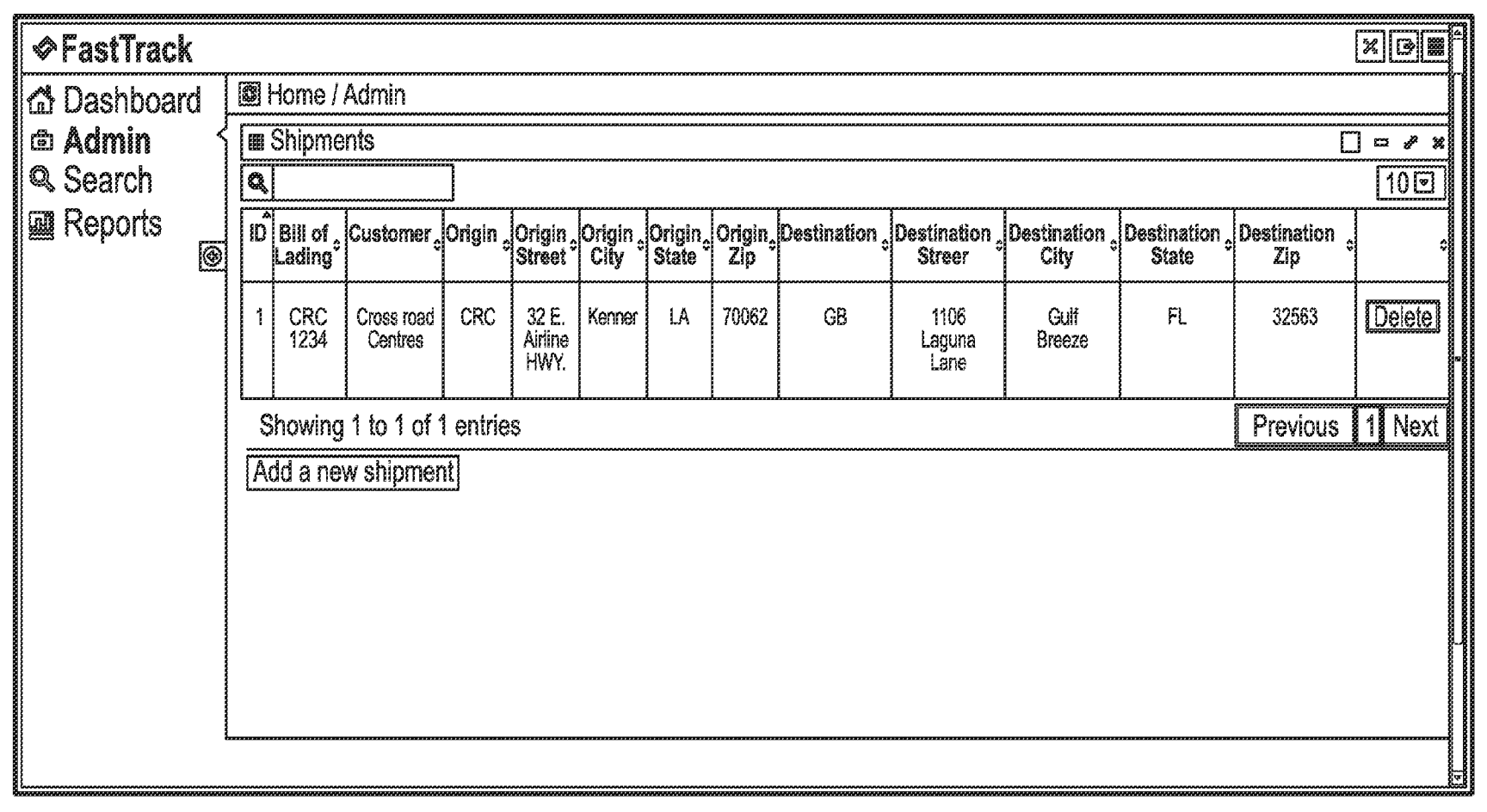

The tracking system software may further include a search function with textual reporting as seen in FIG. 12. Shipment status may be searched for by criterion including, for example, destination address, bill of lading, product, carrier, or customer. The search results may display both active and historical loads. The historical data may allow a user to analyze shipment trends by carrier, customer, or product. The tracking system software may include an administration screen as seen in FIG. 13 that provides the functionality to create/delete/edit products, create/delete/edit shipments, assign a tracking device to a shipment, create alerts, or create geofence.

In various embodiments the tracking system may be integrated into a transportation management system, located on the same computer or operably connected thereto. The transportation management system may take parameters from tracking system and use them to manage other elements related thereto. For instance when generating a cost estimate for a customer the transportation management system can screen recent and ongoing trajectories along the route used to base travel time, fuel use, and cost. When planning a route for delivery of freight, the transportation system can use the detailed information from the tracking system to see what intersections to avoid further optimizing overall delivery and pick up. The transportation system can also use information related to the evolving position of a load to appropriately schedule a drop off time for the load or schedule a check-in at a remote check-in facility as described in U.S. patent application Ser. No. 14/506,545, filed Oct. 3, 2014, which is incorporated herein by reference in its entirety. Embodiments of the present invention as described herein can be integrated with various embodiments described in U.S. patent application Ser. No. 14/506,545.

While the embodiments are described with reference to various implementations and exploitations, it will be understood that these embodiments are illustrative and that the scope of the inventions is not limited to them. Many variations, modifications, additions, and improvements are possible. Further still, any steps described herein may be carried out in any desired order, and any desired steps may be added or deleted. Support for the present invention, including example embodiments of the present invention, may be found in the attached documents and figures, all of which are expressly incorporated herein in their entirety by reference hereto.

What is claimed is:

1. A removable tracking device, comprising:
an accelerometer;
a GPS device;
a wireless communications module;
a power supply;
a housing enclosing the accelerometer, the GPS device, the wireless communications module, and the power supply;
a mounting aperture;
a bolt seal configured to fit within the mounting aperture and securely mount the removable tracking device; and
a locking member configured to couple to the bolt seal to thereby secure the bolt seal and the tracking device to a container,
wherein the removable tracking device is configured to detect a presence or absence of a GSM signal and to configure the wireless communications module for GSM or satellite communications based on the presence or absence of the GSM signal.

2. The removable tracking device as in claim 1, wherein the bolt seal and the locking member create a closed electrical circuit when the locking member is coupled to the bolt seal, the closed electrical circuit including a sensor within the housing.

3. The removable tracking device as in claim 2, wherein the sensor monitors the closed electrical circuit and is configured to detect an open circuit condition.

4. The removable tracking device as in claim 3, wherein the sensor is in communication with the wireless communication module and is configured to transmit detection of the open circuit condition through the wireless communication module to a remote computing device.

5. The removable tracking device as in claim 1, wherein the accelerometer is a vibration sensor.

6. The removable tracking device as in claim 5, wherein the vibration sensor is in communication with the wireless communication module and is configured to transmit motion data through the wireless communication module to a remote computing device.

7. The removable tracking device as in claim 1, further comprising a rigid support member with a connector at a first end, and wherein the mounting aperture is formed in the connector.

8. The removable tracking device as in claim 7, wherein the rigid support member has a second end attached to the housing, wherein the connector is configured to securely attach to the bolt seal such that the bolt seal cannot be removed from the rigid support member without breaking the bolt seal.

9. The removable tracking device as in claim 1, wherein the GPS device is configured to transmit, through the wireless communication module, location information to a remote computing device.

10. The removable tracking device as in claim 1, further comprising a temperature sensor, the temperature sensor coupled to the wireless communication module and configured to send temperature data to a remote computing device.

11. A system, comprising:
a removable tracking device, comprising:
a GPS device;
a wireless communications module configured to:
determine an availability of a GSM signal;
send data over the GSM signal when the GSM signal is available; and
send data over a satellite signal when the GSM signal is unavailable; and
a housing enclosing the GPS device and the wireless communications module;
a seal configured to attach the removable tracking device to a container;
a locking member configured to engage with the seal to secure the seal and the removable tracking device to the container; and
a remote computing device in communication with the removable tracking device.

12. The system as in claim 11, wherein the removable tracking device further comprises an accelerometer.

13. The system as in claim 11, further comprising a mounting member carried by the housing.

14. The system as in claim 13, wherein the mounting member includes an aperture.

15. The system as in claim 14, wherein the seal is configured to fit through the aperture and the locking member is configured to engage with the seal to inhibit the seal from being removed from the aperture.

16. A system, comprising:
a tracking device, the tracking device comprising:
a GPS device; and
a wireless communications module configured to:
determine an availability of a GSM signal;
send data over the GSM signal when the GSM signal is available; and
send data over a satellite signal when the GSM signal is unavailable;
a seal configured to attach the tracking device to a container;
a locking member configured to engage with the seal to secure the seal and the tracking device to the container; and
a remote computing device in communication with the tracking device.

17. The system as in claim 16, wherein the GPS device continuously sends location data to the remote computing device.

18. The system as in claim 16, further comprising a vibration sensor, and where the vibration sensor is configured to send motion data to the remote computing device.

19. The removable tracking device as in claim 1, wherein the removable tracking device is configured to encrypt tracking information transmitted from the removable tracking device.

20. The system as in claim 16, wherein the tracking device is configured to encrypt tracking information transmitted from the tracking device.

* * * * *